(12) United States Patent
Patil et al.

(10) Patent No.: US 12,011,495 B2
(45) Date of Patent: Jun. 18, 2024

(54) LONG WEAR LIQUID ANHYDROUS COMPOSITION

(71) Applicant: CHANEL INC, New York, NY (US)

(72) Inventors: Anjali Patil, Piscataway, NJ (US); Eileen Kim, Piscataway, NJ (US)

(73) Assignee: CHANEL INC, New York, NY (US)

(*) Notice: Subject to any disclaimer, the term of this patent is extended or adjusted under 35 U.S.C. 154(b) by 122 days.

(21) Appl. No.: 17/557,105

(22) Filed: Dec. 21, 2021

(65) Prior Publication Data

US 2023/0190605 A1 Jun. 22, 2023

(51) Int. Cl.
| | |
|---|---|
| *A61K 8/37* | (2006.01) |
| *A61K 8/25* | (2006.01) |
| *A61K 8/31* | (2006.01) |
| *A61K 8/34* | (2006.01) |
| *A61Q 1/06* | (2006.01) |

(52) U.S. Cl.
CPC ............... *A61K 8/375* (2013.01); *A61K 8/25* (2013.01); *A61K 8/31* (2013.01); *A61K 8/345* (2013.01); *A61Q 1/06* (2013.01); *A61K 2800/432* (2013.01)

(58) Field of Classification Search
None
See application file for complete search history.

(56) References Cited

U.S. PATENT DOCUMENTS

2003/0108502 A1* 6/2003 Uchida .................. A61K 8/345
424/70.11

* cited by examiner

*Primary Examiner* — Danah Al-Awadi
(74) *Attorney, Agent, or Firm* — Maier & Maier, PLLC

(57) ABSTRACT

A liquid anhydrous composition including (a) at least one water soluble dye, (b) at least one polyol, and (c) a polyglyceryl-10 pentaoleate, (d) at least one volatile oil, wherein the relative mass amount of (a)/(b)/(c) is ranging between $1/0.6/8 \leq (a)/(b)/(c) \leq 1/6/18$, and a method for preparing the liquid anhydrous composition.

14 Claims, No Drawings

LONG WEAR LIQUID ANHYDROUS COMPOSITION

FIELD

The invention relates to the field of cosmetic products, and more particularly long wear liquid cosmetic compositions allowing for improving the intensity of the color of the makeup and the long-lasting of their intense color. These cosmetic products can for example be used as liquid lipsticks formulations.

BACKGROUND

The use of lipsticks as means for colouring lips has undergone rapid growth, such that lipsticks are now widespread beauty products. Originally, lipstick compositions were solid products melting on the lips upon application but with the growth of the lip makeup market, different textures from liquid to solid have been developed. Independently of its texture, a cosmetically acceptable lipstick should have a homogeneous colour and exhibit long wear properties.

In order to be attractive for the costumer, it is also desirable to offer one lip product under an expanded range of shades. However, colouring materials are either compatible with the water phase (dyes) or with the oily phase (pigments). It is for example complicated to combine dyes and pigments in anhydrous compositions since water-soluble dyes are incompatible in anhydrous compositions. In order to incorporate water soluble dyes in fatty continuous phase compositions, document WO 2017/162599 for example discloses formulating an emulsion, where the dispersed water phase contains a water-soluble dye. The incorporation of dyes in aqueous dispersed phases of emulsions often leads to bleeding of dyes resulting in non-uniform formulas.

Formulating liquid compositions containing pigments and dyes while having a uniform color and a low viscosity (below 300 mPa·s) remains a technical challenge.

Furthermore, when long wear properties are sought, it is conventional to use volatile oils that will evaporate rapidly after application of the makeup and therefore leave a non-greasy and long-lasting coloured film on the lips. However, the presence of volatile oils further decreases the viscosity of liquid formulations which renders the suspension of pigments even more complicated and can affect the homogeneity of the formulation.

SUMMARY

It is therefore an objective of the present invention to provide a low viscosity liquid anhydrous composition comprising at least one water soluble dye, where said water soluble dye is homogeneously dispersed, and wherein the liquid anhydrous composition exhibits long wear properties, intensity of colour and long-lasting of the intense color.

It is indeed of the merits of the applicant to have discovered that water soluble dyes could be homogeneously and stably incorporated into low viscosity liquid anhydrous compositions, in the presence of at least one volatile oil, when combined with a specific surfactant, namely polyglyceryl-10 pentaoleate, and a polyol in a particular mass proportion.

Thus, the invention relates according to a first aspect, to a liquid anhydrous composition comprising:
(a) at least one water soluble dye,
(b) at least one polyol, and
(c) a polyglyceryl-10 pentaoleate
(d) at least one volatile oil,
wherein the relative mass amount of (a)/(b)/(c) is ranging between $1/0.6/8 \leq (a)/(b)/(c) \leq 1/6/18$.

The liquid anhydrous composition of the invention can be any makeup product for application to the keratinous materials, in particular skin or nails. In a preferred embodiment, the liquid anhydrous composition of the invention is a lip product, such as a liquid lipstick or a lipgloss.

The invention also relates, according to a further aspect, to a method for the preparation of said liquid anhydrous composition comprising the flowing steps:
 i. preparing a premix of
  (a) at least one water soluble dye,
  (b) at least one polyol, and
  (c) polyglyceryl-10 pentaoleate
 ii. incorporating of at least one volatile oil (d) and all other optional ingredients into the premix.

DETAILED DESCRIPTION

Within the meaning of the invention, the term "liquid composition" intends to mean a composition that flows under its own weight, as opposed to a solid composition.

In a preferred embodiment, the liquid anhydrous composition of the invention has a viscosity, as measured on TA Instruments DHR2 rheometer. Mobile: 40 mm smooth cone and 4° angle; 96 µm air gap; 40 mm smooth support. Method: rotation at 100 s-1 for 120 s at 25° C., after a warm-up time of 60 s., between 1 to 300 mPa·s, preferably between 20 and 150 mPa·s.

The composition of the invention is anhydrous. Within the meaning of the invention, the term "anhydrous composition" intends to mean a composition comprising very low amounts of water, in particular less than 5% by weight, with respect to the total weight of the composition, preferably less than 3% by weight, and more preferably less than 1% by weight of water. In a preferred embodiment, the composition of the invention is free from water.

Water Soluble Dye

The composition of the invention comprises at least one water soluble organic dye. The water-soluble dye can either be natural or of natural origin, or can be an organic dye "Natural compound" means a compound that is obtained directly from the earth or the soil, or from plants or animals, via, where appropriate, one or more physical processes, for instance milling, refining, distillation, purification or filtration, or else resulting from a biotechnological process, especially resulting from cell or microbiological cultures, for example of fungi or of bacteria.

"Compound of natural origin" means a natural compound that has undergone one or more additional chemical or industrial treatments, giving rise to modifications that do not affect the essential qualities of this compound and/or a compound predominantly comprising natural constituents that may or may not have undergone transformations as indicated above. Mention may be made, as nonlimiting example of additional chemical and industrial treatment bringing about modifications which do not affect the essential qualities of a natural compound, of those allowed by the controlling bodies such as Ecocert (Reference system for biological and ecological cosmetic products, January 2003), or defined in recognized handbooks in the field, such as Cosmetics and Toiletries Magazine, 2005, Vol. 120, 9: 10.

According to the invention, a compound is considered to be natural or of natural origin when it is predominantly composed of natural constituents, that is to say when the weight ratio of natural constituents to non-natural constituents which make up the compound is greater than 1.

"Water-soluble dye", and more generally a "water-soluble compound" means a dye or compound which has a solubility in water, measured at 25° C., at least equal to 0.01 g/l (production of a macroscopically isotropic, transparent, colored or colorless solution).

By way of water-soluble dyes suitable for the invention, the following may especially be mentioned: water-soluble natural dyes such as, for example, betanin (beetroot), carmine, copper chlorophyllin, methylene blue, ortho-diphenol derivatives such as anthocyanins (radish, red cabbage, purple yam, purple corn, black carrot, hibiscus, elderberries), caramel, sandalwood, gardenia, spirulina and riboflavin.

It is more particularly a natural ortho-diphenol derivative.

The ortho-diphenols which may be used according to the invention are preferably chosen from anthocyanidins, such as cyanidin, delphinidin and petunidin; anthocyanins or anthocyans, such as myrtillin; proanthocyanidins and especially the proanthocyanidins A1, A2, B1, B2, B3 and CI; proanthocyanins and mixtures of the previous compounds.

In a preferred embodiment, the water-soluble dye is a water-soluble organic dye.

The water soluble organic dye can be chosen from CI 12085 (RED 36), CI 15850 (RED 6), CI 15850 (RED 7) [E180], CI 15985 (YELLOW 6) [E110], CI 17200 (RED 33), CI 19140 (YELLOW 5) [E102], CI 42090 (BLUE 1) [E133], CI 45370 (ORANGE 5), CI 45370 (ORANGE 5), CI 45380 (RED 22), CI 45410 (RED 27), CI 45410 (RED 28), CI 47000 (YELLOW 11), CI 47005 (YELLOW 10) [E104], CI 61570 (GREEN 5), Acid Red 18, CI 16255, Red 21, CI 45380, and mixtures thereof.

For obvious reasons, the amount of this dye or mixture of dyes present in a composition according to the invention is able to vary significantly with regard to the hue range and the chromatic intensity sought by its presence.

By way of illustration, a composition according to the invention may comprise from 0.01% to 10% by weight, relative to the total weight of the composition, preferably from 0.1% to 5% by weight, and more preferably 0.5% to 3% by weight of water-soluble dyes.

According to another embodiment, the composition according to the invention contains at least one ortho-diphenol derivative, and preferably at least one anthocyanin derivative, as water-soluble natural dye.

Other Colouring Agents

In one embodiment of the invention, the liquid anhydrous composition comprises at least one coloring agent other than the water-soluble dye.

The colouring agent may particularly be chosen from among liposoluble colorants, pigments, nacres or one of the mixtures thereof. Preferably, Examples of mineral pigments are particularly titanium dioxide, iron, zinc or chromium oxides, manganese violets, ultramarines, ferric ferrocyanide known as Prussian Blue, as well as composite pigments and goniochromatic, pearlescent, interferential, photochromic or thermochromic pigments, without this list being exhaustive.

Examples of organic pigments suitable for use in the invention are particularly carbon black, D&C type pigments, FD & C type pigments lacquers based on cochineal carmine, barium, strontium, calcium or aluminium or indeed diketopyrrolopyrrole (DPP) described in the documents EP-A-542669, EP-A-787730, EP-A-787731 and WO-A-96/08537.

The nacres may be chosen from among those conventionally present in makeup products, such as micas/titanium dioxide. Alternatively, they may consist of nacres based on mica/silica/titanium dioxide, based on synthetic fluorphlogopite/titanium dioxide (MAPRECOS SUNSHINE®), calcium sodium borosilicate/titanium dioxide (ENGELHARD REFLECKS®) or calcium aluminium borosilicate/silica/titanium dioxide (MERCK RONASTAR®).

These colouring agents other than the water-soluble dye may be optionally surface-treated with a hydrophobic agent such as silanes, silicones, fatty acid soaps, $C_{9-15}$ fluoroalcohol phosphates, acrylate/dimethicone copolymers, mixed $C_{9-15}$ fluoroalcohol phosphate/silicone copolymers, lecithins, carnauba wax, polyethylene, chitosan and optionally acylated amino acids such as lauroyl lysine, disodium stearoyl glutamate and aluminium acyl glutamate.

The colouring agents other than the water-soluble dye can be present in the composition at a content of between 3% and 10% by weight with respect to the total weight of the composition.

Polyol

The liquid anhydrous composition of the invention also comprises at least one polyol.

Preferably, a polyol in accordance with the present invention is present in liquid form at room temperature.

The polyols that are advantageously suitable for the formulation of a composition according to the present invention are those especially containing from 2 to 32 carbon atoms, preferably 3 to 16 carbon atoms and in particular from 3 to 7 carbon atoms.

Advantageously, the polyol may be chosen, for example, from ethylene glycol, pentaerythritol, trimethylolpropane, propylene glycol, 1,3-propanediol, butylene glycol, isoprene glycol, pentylene glycol, hexylene glycol, glycerol, polyglycerols such as glycerol oligomers, for instance diglycerol, caprylyl glycol, and polyethylene glycols, and mixtures thereof, in particular glycerol.

More preferably, the polyol is chosen from glycerol, butylene glycol, pentylene glycol, hexylene glycol, caprylyl glycol, and mixtures thereof, and preferably glycerol.

The polyol may be used in an amount ranging from 0.01% to 5% by weight, preferably from 0.1% to 3% by weight and even more preferentially from 0.2% to 1% by weight of polyol relative to the total weight of the composition.

Polyglyceryl-10 Pentaoleate

The liquid anhydrous composition of the invention also comprises a polyglyceryl-10 pentaoleate.

This polyglyceryl fatty acid ester of oleic acid comprises 10 glycerol units and has a HLB value: 3.5 and is for example available under the commercial reference Nikkol Decaglyn 5-OV from NIKKO CHEMICALS Co. LTD.

The amount of polyglyceryl-10 pentaoleate in the composition according to the present invention may be 1% to 20% by weight, preferably 2% to 15% by weight, and more preferably 3% to 13% by weight, relative to the total weight of the composition.

The Oils

The liquid anhydrous composition of the invention also comprises at least one volatile oil.

According to the present invention, the term "oil" denotes a liquid compound at ambient temperature (25° C.), and which, when introduced at a rate of at least 1% by weight into water at 25° C., is not at all soluble in water, or soluble at a rate of less than 10% by weight, with respect to the weight of oil introduced into the water.

Volatile Oil

"Volatile oil" denotes an oil suitable for evaporating in contact with skin in less than one hour, at ambient temperature and atmospheric pressure.

The volatile oil is a volatile cosmetic oil, liquid at ambient temperature, having particularly a non-zero vapour pressure at ambient temperature and atmospheric pressure, in particular having a vapour pressure of between 0.13 Pa and 40,000 Pa (0.001 to 300 mm of Hg), preferably between 1.3 Pa and 13,000 Pa (0.01 to 100 mm of Hg), and more preferentially between 1.3 Pa and 1,300 Pa (0.01 to 1,000 mm of Hg).

The volatile oils comprise volatiles silicone oils and/or volatile hydrocarbon oil.

The volatile silicone oils optionally used in the compositions according to the invention are linear or cyclic, have particularly from 2 to 7 silicon atoms, optionally alkyl or alkoxy groups having from 1 to 10 carbon atoms, and having a viscosity, at ambient temperature, less than 5 cSt.

By way of examples of volatile silicone oil, mention may more particularly be made of hexamethylcyclotrisiloxane, octamethylcyclotetrasiloxane, decamethylcyclopentasiloxane, dodecamethylcyclohexasiloxane, cyclotetradimethylsiloxane, cyclopentadimethylsiloxane, cyclohexadimethylsiloxane, hexamethyldisiloxane, octamethyltrisiloxane, hexylheptamethyltrisiloxane, octylheptamethyltrisiloxane, decamethyltetrasiloxane, dodecamethylpentasiloxane, heptamethylhexyl trisiloxane, heptamethyloctyl trisiloxane or one of the mixtures thereof.

The hydrocarbon volatile oil may be chosen from hydrocarbon oils having from 7 to 16 carbon atoms. As a hydrocarbon volatile oil having from 7 to 16 carbon atoms, mention can be made in particular of $C_8$-$C_{16}$ branched alkanes such as $C_8$-$C_{16}$ iso-alkanes (also referred to as isoparaffins), isododecane, isodecane, isohexadecane and for example the oils sold under the trade names Isopars or Permetyls, $C_8$-$C_{16}$ branched esters such as iso-hexyl neopentanoate, and mixtures thereof. Preferably, the hydrocarbon volatile oil having from 8 to 16 carbon atoms is chosen from isododecane, isodecane, isohexadecane and mixtures thereof, and is in particular isododecane.

Concerning the volatile hydrocarbon oil, mention may more particularly be made of a short-chain hydrocarbon oil, volatile linear alkanes such as for example described in document FR2933865 incorporated by way of reference.

By way of examples of short-chain hydrocarbon oil(s), mention may particularly be made of that/those chosen in the group comprising isododecane, dodecane or mixtures thereof.

By way of example of volatile linear alkanes, mention may be made of those hydrocarbon chains in:

C9-C17, C10-C14, such as a mixture of undecane ($C_{11}$) and tridecane ($C_{13}$), marketed by BASF Care Creations under the trade name Cetiol® Ultimate, C15-19, such as those marketed by Seppic under the trade name Emogreen L15, C12-14, such as those marketed by Biosynthis under the trade name Vegelight 1214LC, n-dodecane (C12) marketed by Sasol under the tradename Parafol 12-97 and n-tetradecane (C14) marketed by Sasol under the tradename Parafol 14-97, C9-12 alkane, such as those marketed by Daito under the trade name Makigreen D10 or those marketed by Biosynthis under the tradename Vegelight Silk.

In a preferred embodiment, the volatile oil is chosen from isododecane, the mixture of n-undecane ($C_{11}$) and n-tridecane ($C_{13}$), dodecane, or mixtures thereof.

The volatile oil is present in an amount between 20% and 99% by weight, relative to the total weight of the composition, preferably between 20 and 49% by weight, and wherein the mass amount of (a)+(b)+(c) represents from 1 to 80% of the total weight of the composition, preferably from 1 to 60% by weight.

Non-Volatile Oil

The liquid anhydrous composition of the invention can also comprise at least one non-volatile oil.

"Non-volatile oil" denotes an oil which has a boiling point generally greater than 300° C. under 760 mm of Hg (101325 Pa) and which has little or no vapour tension.

The non-volatile oils may particularly be chosen from among non-volatile silicon oils, non-volatile hydrocarbon oils, and mixtures thereof.

"Silicone oil" denotes an oil comprising at least one silicon atom, and particularly at least one Si—O group.

As a non-volatile silicone oil, mention may particularly be made of polydimethylsiloxanes containing at least 8 silicon atoms, polyalkylmethylsiloxanes wherein the alkyl chain contains from 8 to 20 carbon atoms and the oils identified by the INCI name phenyl trimethicone.

"Hydrocarbon oil" denotes an oil containing only hydrogen and carbon atoms.

Mention may be made for example of hydrocarbons such as squalane, phytosqualane, polybutene, hydrogenated polyisobutene, hydrogenated polydecene, synthetic (poly) esters also known as "ester oils" and (poly) ethers, in particular C6-C20 acid and C6-C20 alcohol (poly) esters, advantageously branched such as isononyl isononanoate; plant oils; branched and/or unsaturated fatty acids; branched and/or unsaturated fatty alcohols such as octyldodecanol; or one of the mixtures thereof.

"Ester oil" denotes a mono-, di-, tri- or tetra-ester oil. The ester oils are obtained by reacting a mono-, di-, tri- and more generally a polyol with a mono- di- tri- and more generally a carboxylic polyacid, said reagents optionally being linear or branched, saturated or unsaturated, aliphatic or aromatic, and optionally comprising alkoxylated groups. The ester oils may particularly be hydroxylated.

In particular, the non-volatile ester oil may comprise from 18 to 70 carbon atoms.

The non-volatile ester oil may particularly be chosen from among:

monoesters comprising 18 to 40 carbon atoms, in particular monoesters of formula R1COOR2 wherein R1 represents the residue of a linear or branched fatty acid comprising from 6 to 20 carbon atoms and R2 represents a hydrocarbon chain, particularly branched, containing from 6 to 20 carbon atoms, such as for example Purcellin oil (cetostearyl octanoate), isononyl isononanoate, isodecyl neopentanoate, C12 to C15 alkyl benzoates, 2-ethylhexyl palmitate, octyldodecyl neopentanoate, 2-octyldodecyl stearate, 2-octyldodecyl erucate, isostearyl isostearate, 2-octyldodecyl benzoate, alkyl octanoates, decanoates or ricinoleates, isopropyl myristate, isopropyl palmitate, butyl stearate, hexyl laurate, 2-ethylhexyl palmitate, 2-hexyldecyl laurate, 2-octyldecyl palmitate, 2-octyldodecyl palmitate, 2-diethylhexyl succinate;

diesters comprising 18 to 60 carbon atoms, in particular from 18 to 50 carbon atoms, such as diesters of carboxylic acid and monoalcohols, such as diisostearyl malate; diesters of glycol and carboxylic monoacids, such as neopentylglycol diheptonoate, polyglyceryl-2 diisostearate, triesters comprising 35 to 70 carbon atoms, such as triesters of carboxylic triacid, such as triisostearyl citrate or tridecyl trimellitate; or triesters of glycol and carboxylic monoacids such as polyglyceryl-2 triisostearate;

tetraesters comprising 35 to 70 carbon atoms, such as such as tetraesters of penthaerythritol or polyglycerol and a carboxylic monoacid, for example pentaerythrityl tetrapelargonate, pentaerythrityl tetraisostearate, pentaerythrityl tetraisononanoate, glyceryl tridecyl-2 tetradecanoate, polyglyceryl-2 tetraisostearate or indeed pentaerythrityl tetradecyl-2 tetradecanoate; pentaerithrityl adipate/caprate/caprylate/heptanoate polyesters obtained by condensation of dimer and/or trimer of unsaturated fatty acid and diol such as polyglyceryl-2 isostearate/dimerdilinoleate copolymer marketed by the company Estenity under the tradename Hailucent ISDA or the polyester of dilinoleic acid and 1,4-butanediol;

esters and polyesters of dimer diol and mono- or dicarboxylic acid, such as the esters of dimer diol and fatty acid and the esters of dimer diols and carboxylic diacid dimer, in particular those obtained from a dimer of a C8 to C34, particularly C12 to C22, in particular C16 to C20, and more particularly C18 unsaturated fatty acid, such as the esters of dilinoleic diacids and dilinoleic dimer diols, for example those marketed by the company NIPPON FINE CHEMICAL under the trade name LUSPLAN DD-DA5® and DD-DA7®;

triglycerides of fatty acids (liquid at ambient temperature), particularly of fatty acids having from 7 to 40 carbon atoms, such as heptanoic or octanoic acid triglycerides or jojoba oil; saturated triglycerides such as caprylic/capric triglyceride, glyceryl triheptanoate, glycerin trioctanoate; C18-36 acid triglycerides such as those marketed under the reference DUB TGI 24 marketed by Stéarineries Dubois); C10-18 triglyceride, glyceryl dioleate, C8-12 acid triglyceride and unsaturated triglycerides such as castor oil, olive oil, ximenia oil, pracaxi oil;

or one of the mixtures thereof.

An additional non-volatile oil may also be used to add further properties to the composition according to the invention.

By way of example, diisostearyl malate, polyglyceryl-3 diisostearate, polyglyceryl-2 triisostearate, pentaerythrityl adipate/caprate/caprylate/heptanoate may be added as it makes it possible to obtain good pigment dispersion.

Further additional oils may be added to enhance the sensory properties of the formula.

According to an embodiment, the non-volatile oil is chosen from among hydrogenated polyisobutene, polyglyceryl-2 triisostearate, polyglyceryl-3 diisostearate, diisostearyl malate, octyldodecanol, isostearyl isostearate, pentaerythrityl adipate/caprate/caprylate/heptanoate C10-18 triglyceride, glyceryl dioleate, C8-12 acid triglyceride and polyglyceryl-2 isostearate/dimerdilinoleate copolymer or one of the mixtures thereof.

According to a particular embodiment of the invention, the non-volatile oil introduced into the composition according to the invention is a mixture of hydrogenated polyisobutene, polyglyceryl-2 triisostearate, diisostearyl malate, octyldodecanol and isostearyl isostearate.

The non-volatile oil may be present in the composition according to the invention at a content of between 10% and 40% by weight, preferably between 15% and 35% by weight, more preferentially between 20% and 30% by weight, with respect to the weight of the composition.

Additional Ingredients

The liquid anhydrous composition of the invention may also comprise additional ingredients such as structuring agents such as a wax and/or at least a lipophilic gelling agent, film-forming agents, active ingredients, fillers, preservatives or mixtures thereof.

According to an embodiment, the film-forming agent is chosen from among silicon resins such as trimethylsiloxysilicate as those markeketed by the company Wacker under the tradename Belsil TMS803, or dextrin esters such as dextrin isostearate & C8-12 acid triglyceride & isododecane as those marketed by the company Chiba Flour Milling under the tradename Unifilma HVY The preservatives should be chosen with particular care to avoid any interaction with the water-soluble dye.

Method

The present invention also relates to providing a method for for the preparation of a liquid anhydrous composition as previously disclosed, comprising the flowing steps:
i. preparing a premix of
  (a) at least one water soluble dye,
  (b) at least one polyol, and
  (c) polyglyceryl-10 pentaoleate
   wherein the relative mass amount of (a)/(b)/(c) is ranging between $1/0.6/8 \leq (a)/(b)/(c) \leq 1/6/18$,
ii. incorporating of at least one volatile oil (d) and all other optional ingredients into the premix.

The following examples are given to illustrate the invention. These examples merely being given by way of illustration, the invention may in no way be restricted to the subject matter thereof.

Example I

The liquid anhydrous compositions of the following formulas (% by weight) were prepared:

TABLE 1

| Fonction | INCI name | Trademark (company) | Comparative example B1 % | Comparative example B2 % | Comparative example B3 % | Comparative example B4 % | Example of the invention B5 % |
|---|---|---|---|---|---|---|---|
| hydrosoluble organic dye | CI 15985 (YELLOW 6) | UNICERT YELLOW 08006-J | 0.6 | 0.6 | 0.6 | 0.6 | 0.6 |
| hydrosoluble organic dye | CI 17200 (RED 33) | UNICERT RED K7057-J | 0.29 | 0.29 | 0.29 | 0.29 | 0.29 |

TABLE 1-continued

| Fonction | INCI name | Trademark (company) | Comparative example B1 % | Comparative example B2 % | Comparative example B3 % | Comparative example B4 % | Example of the invention B5 % |
|---|---|---|---|---|---|---|---|
| hydrosoluble organic dye | CI 45410 (RED 28) | UNICERT RED K7054-J | 0.42 | 0.42 | 0.42 | 0.42 | 0.42 |
| Humectant | glycerin | | 12.48 | 6.7 | 1.04 | 1.04 | 1.04 |
| Surfactant | Polyglycerin-10 pentaoleate | Decaglyn 5OV (Nikko Chemicals Co. LTD | 0 | 5.78 | 0 | 0 | 11.44 |
| Non volatil oil | Polyglyceryl-3 Diisostearate | Cithrol PG 32 IS LQ MV (Croda) | 0 | 0 | 11.44 | 0 | 0 |
| Non volatil oil | Polyglyceryl-3 Polyricinoleate | Imwittor 600 (IOI OLEO GMBH) | 0 | 0 | 0 | 11.44 | 0 |
| Volatile oil | isododecane | | 86.21 | 86.21 | 86.21 | 86.21 | 86.21 |
| | Total (%) | | 100 | 100 | 100 | 100 | 100 |

Procedure:

All the dyes were weighted and mixed. The humectant, the surfactant and/or non-volatile oil depending on the formula were further added, mixed well and heated to 95° C. for 1 hour while mixing. The mixture was then allowed to cool down to room temperature. Isododecane was then added to the cooled solution while mixing to obtain a homogeneous composition.

Viscosity for Example B5: 2.07 mPa·s

Viscosity of only dye solution without isododecane: 13821 mPa·s

Procedure for measuring viscosities: Instrument: TA Instruments DHR2 rheometer. Mobile: 40 mm smooth cone and 4° angle; 96 µm air gap; 40 mm smooth support. Method: rotation at 100 s-1 for 120 s at 25° C., after a warm-up time of 60 s.

The composition of Example B5 of the invention provides a mixture which is homogeneous, stable at room temperature for 1 month.

The composition of comparative example B1 comprising a volatile oil (isododecane) but no polyglyceryl-10 pentaoleate results in a solution which is not homogeneous and shows two immiscible phases.

The formula of comparative example B2, comprising relative mass amount of (a)/(b)/(c) outside of the claimed scope, provides a solution which is not homogeneous and shows liquid on top after mixing.

The formula of comparative example B3, using polyglyceryl-3 diisostearate instead of polyglycerin-10 pentaoleate results in a composition which is not homogeneous after mixing: the dye did not dissolve and formed aggregates.

The formula of comparative example B4, using polyglyceryl-3 polyricinoleate instead of polyglycerin-10 pentaoleate results in a composition which is not homogeneous and shows liquid on top after mixing.

Example II

| Fonction | INCI name | Trademark (company) | % of ingredient |
|---|---|---|---|
| hydrosoluble organic dye | CI 15985 (YELLOW 6) | UNICERT YELLOW 08006-J | 0.23 |
| hydrosoluble organic dye | CI 17200 (RED 33) | UNICERT RED K7057-J | 0.11 |
| hydrosoluble organic dye | CI 45410 (RED 28) | UNICERT RED K7054-J | 0.16 |
| Humectant | glycerin | | 0.38 |
| surfactant | Polyglycerin-10 pentaoleate | Nikkol Decaglyn 5OV (Nikko Chemicals Co. LTD | 4.38 |
| Non volatil oil | Hydrogenated polyisobutene & tocopherol | Parleam 3 (Rossow) | 0.75 |
| Non volatil oil | Polyglyceryl-2 triiisostearate | Salacos 43 V (MB) (Saci CPFA) | 3 |
| Non volatil oil | Diisostearyl malate | | 16.66 |
| Non volatil oil | octyldodecanol | Eutanol-G | 7 |
| Non volatil oil | Isostearyl isostearate | Crodamol Isis LQ (MV) (Croda) | 1.7 |
| Active | C10-18 TRIGLYCERIDES & SODIUM HYALURONATE & TRIOLEIN & GLYCERYL DIOLEATE | TECHNOHYAL HYAPEARL (Roelmi HPC SRL) | 0.3 |
| Oil gellant | Isododecane (12.18%) & disteardimonium hectorite (1.4%) & propylene carbonate (0.42%) | Bentone gel ISDV (Elementis) | 14 |
| Film-forming agent | VP/Hexadecene copolymer | Unimer U-151 | 4.5 |
| Film-forming agent | polybutene | Indopol H-100 | 8.5 |
| Film-forming agent | Trimethylsiloxysilicate | Belsil TMS 803 | 9 |
| inorganic & organic pigments | | | 5.7 |

-continued

| Fonction | INCI name | Trademark (company) | % of ingredient |
|---|---|---|---|
| Optical effect Filler | silica | Creaspheres Sil WL9 (cosmo Chem SARL) | 2 |
| Hydratant | actif | | 0.3 |
| Anti-oxydant | Tocopheryl acetate | | 0.5 |
| Volatile oil | Total isododecane (including bentone solvant) | | 33.06 |
| | Total (%) | | 100 |

The liquid anhydrous composition of the following formula (% by weight) was prepared:
Procedure:
1) Pre-mix octyldodecanol with VP/Hexadecene copolymer.
2) Add isostearyl isostearate, hydrogenated polyisobutene & tocopherol, polybutene, Polyglyceryl-2 triiisostearate and C10-18 TRIGLYCERIDES & SODIUM HYALURONATE & TRIOLEIN & GLYCERYL DIOLEATE and heat to 70° C., and mix well.
3) Then turn the heat off and add bentone gel (isododecane (12.18%) & disteardimonium hectorite (1.4%) & propylene carbonate (0.42%)) and mix until Bentone gel is fully dispersed (about 15 min). Then cool down to room temperature to constitute phase 1.
4) Combine all dyes and glycerin and polyglyceryl-10 pentaoleate in a beaker, heat to 95° C. and mix for 1 hour and then cool down to room temperature to constitute phase 2.
5) Add phase 2 to phase 1 and mix for 5-10 min until dyes are well dispersed.
6) Add the pigments to phase 1 and mix for 10 minutes until the pigments are well dispersed.
7) Slowly add silica to phase 1 while mixing and continue mixing for 10 minutes.
8) Pre-disperse trimethylsiloxysilicate into isododecane and slowly pour into phase 1 while mixing and continue mixing for 10 min.
Steps 5-8 are operated at room temperature.
Viscosity of the composition: 84.22 mPa·s
Procedure for measuring viscosities: Instrument: TA Instruments DHR2 rheometer. Mobile: 40 mm smooth cone and 4° angle; 96 μm air gap; 40 mm smooth support. Method: rotation at 100 s-1 for 120 s at 25° C., after a warm-up time of 60 s.

The invention claimed is:
1. A liquid anhydrous composition comprising:
  (a) at least one water soluble dye,
  (b) at least one polyol, and
  (c) a polyglyceryl-10 pentaoleate
  (d) at least one volatile oil,
wherein the relative mass amount of (a)/(b)/(c) is ranging between $1/0.6/8 \leq (a)/(b)/(c) \leq 1/6/18$.
2. The liquid anhydrous composition according to claim 1, wherein the at least one volatile oil is present in an amount between 20% and 99% by weight, relative to the total weight of the composition, and wherein the mass amount of (a)+(b)+(c) represents from 1 to 80% of the total weight of the composition.
3. The liquid anhydrous composition according to claim 1, further comprising (e) at least one non-volatile oil, wherein the amount of at least one non-volatile oil is between 20% and 50% by weight, relative to the total weight of the composition.
4. The liquid anhydrous composition according to claim 1, having a viscosity between 1 to 300 mPa·s.
5. The liquid anhydrous composition according to claim 1, wherein the at least one water-soluble dye is either natural or of natural origin, or is an organic dye.
6. The liquid anhydrous composition according to claim 5, wherein the at least one water soluble organic dye is chosen from CI 12085, CI 15850, CI 15850, CI 15985, CI 17200, CI 19140, CI 42090, CI 45370, CI 45370, CI 45380, CI 45410, CI 45410, CI 47000, CI 47005, CI 61570, Acid Red 18, CI 16255, Red 21, CI 45380, and mixtures thereof.
7. The liquid anhydrous composition according to claim 1, wherein the at least one polyol is chosen among glycerol, butylene glycol, pentylene glycol, hexylene glycol, caprylyl glycol, and mixtures thereof.
8. The liquid anhydrous composition according to claim 7, wherein the at least one polyol is glycerol.
9. The liquid anhydrous composition according to claim 1, wherein the at least one volatile oil is chosen from hydrocarbon oils, silicone oils and mixtures thereof.
10. The liquid anhydrous composition according to claim 9, wherein the at least one volatile oil is chosen from isododecane, the mixture of n-undecane and n-tridecane, dodecane, or mixtures thereof.
11. The liquid anhydrous composition according to claim 3, wherein the at least one non-volatile oil is chosen from isostearyl isostearate, C8-12 acid triglyceride, polyglyceryl-3 diisostearate, polyglyceryl-2 triisostearate, pentaerythrityl adipate/caprate/caprylate/heptanoate, C10-18 triglyceride, glyceryl dioleate, C8-12 acid triglyceride and polyglyceryl-2 isostearate/dimerdilinoleate copolymer or mixtures thereof.
12. The liquid anhydrous composition according to claim 1, further comprising at least one coloring agent chosen from liposoluble colorants, pigments, nacres or one of the mixtures thereof.
13. A method for the preparation of a liquid anhydrous composition according to claim 1, comprising the flowing steps:
  i. preparing a premix of
    (a) at least one water soluble dye,
    (b) at least one polyol, and
    (c) polyglyceryl-10 pentaoleate
    wherein the relative mass amount of (a)/(b)/(c) is ranging between $1/0.6/8 \leq (a)/(b)/(c) \leq 1/6/18$,
  ii. incorporating of at least one volatile oil (d) and all other optional ingredients into the premix.
14. The liquid anhydrous composition according to claim 4, having a viscosity between 20 to 150 mPa·s.

* * * * *